United States Patent [19]

Chu et al.

[11] Patent Number: 6,042,577
[45] Date of Patent: Mar. 28, 2000

[54] RETENTION MECHANISM FOR CATHETER WITH DISTAL ANCHOR

[75] Inventors: Michael S. H. Chu, Brookline; Yem Chin, Burlington, both of Mass.

[73] Assignee: Boston Scientific Corporation, Natick, Mass.

[21] Appl. No.: 09/249,487

[22] Filed: Feb. 12, 1999

Related U.S. Application Data

[63] Continuation of application No. 08/921,285, Aug. 29, 1997, Pat. No. 5,928,208.
[51] Int. Cl.[7] .................................................. A61M 25/00
[52] U.S. Cl. ........................................... 604/523; 604/533
[58] Field of Search .................................. 604/523, 525, 604/528, 533, 534, 535, 264, 95, 500

[56] References Cited

U.S. PATENT DOCUMENTS

| | | |
|---|---|---|
| 4,643,720 | 2/1987 | Lanciano . |
| 4,740,195 | 4/1988 | Lanciano . |
| 4,846,175 | 7/1989 | Frimberger . |
| 5,030,204 | 7/1991 | Badger et al. . |
| 5,041,085 | 8/1991 | Osborne et al. . |
| 5,185,004 | 2/1993 | Lashinski . |
| 5,419,764 | 5/1995 | Roll . |
| 5,522,400 | 6/1996 | Williams . |
| 5,928,208 | 7/1999 | Chu et al. ............................. 604/523 |

FOREIGN PATENT DOCUMENTS

WO 96/34560  11/1996  WIPO .

*Primary Examiner*—John D. Yasko
*Attorney, Agent, or Firm*—Finnegan, Henderson, Farabow, Garrett & Dunner, L.L.P.

[57] ABSTRACT

A mechanism for use with an anchoring structure of a drainage catheter. A suture thread as a flexible link extends from the distal end of a catheter through the catheter lumen to the mechanism at the proximal end of the catheter. The mechanism includes a distal body affixed to the proximal end of the catheter and a proximal body that can be displaced axially with respect to the distal body between clamping and unclamped positions. In a clamped position, the bodies clamp the suture thread to prevent inadvertent displacement of the suture thread. Displacement of the proximal body in certain embodiments takes up slack in the suture thread generated when the anchor forms.

28 Claims, 7 Drawing Sheets

RETENTION MECHANISM FOR CATHETER WITH DISTAL ANCHOR

This is a continuation of application Ser. No. 08/921,285, filed Aug. 29, 1997 now U.S. Pat. No. 5,928,208.

BACKGROUND OF THE INVENTION

1. Field of the Invention

This invention generally relates to the field of catheters and more particularly to a catheter having a mechanism for retaining a distal end of the catheter in a predetermined configuration.

2. Description of Related Art

There are a variety of therapies or treatment modalities that require a catheter with a distal anchor or the like to retain the catheter in position. One particular application involves catheters used for drainage purposes. For example, procedures for the suprapubic catheterization of the bladder drain the bladder after surgery or when the genitourinary system is plugged by an obstruction. Procedures using other percutaneously inserted catheters are also used to drain the kidney or biliary system as well as to drain abscesses, other sites of fluid collection and other viscera. Still other procedures use percutaneously inserted catheters as gastrostomy feeding tubes.

Generally these catheters are introduced into a patient through a large hypodermic needle or trocar. A guidewire is inserted through the needle or trocar which is then removed. The catheter tube, with a stiffening cannula, passes over the guidewire into the cavity. The cannula and guidewire can then be withdrawn leaving a portion of the catheter at its distal end in the desired cavity.

It is very easy to withdraw one of these catheters by movement of the body or under other conditions. Also these catheters generally have side ports at the distal end that can be inadvertently drawn into the abdominal cavity creating potential for severe infections when the catheter is inserted for bladder treatment.

Various catheters have been developed with diverse anchor structures to prevent inadvertent removal of the catheter. One such anchor is a "pigtail loop" formed by a flexible tube portion at the distal end of the catheter. The loops have a number of ports to ensure drainage. The pigtail loop configuration prevents accidental removal of the catheter from the patient. Generally the pigtail loop is preformed in the catheter because the flexible tube of the catheter is formed of a memory material. For introduction into a patient, a stiff cannula or similar implement is inserted through the catheter lumen to straighten the pigtail loop. The distal end of the flexible tube returns to the pigtail loop configuration after the cannula is removed. Typically a suture thread extends through draw ports at two spaced positions along the distal portion of the flexible tube. These portions come into juxtaposition when the pigtail loop forms after the physician removes the cannula. Then the physician will take up any slack in the one or more suture threads that lead proximally from the pigtail loop. When a suture thread is made taut, it prevents the pigtail loop from straightening by holding the juxtaposed portions of the catheter together. If only a portion of the suture thread is drawn proximally, the suture thread will still prevent the pigtail loop from straightening completely.

When it is appropriate to remove the catheter, a stiff cannula is inserted through the lumen past the suture threads until the cannula reaches the pigtail loop. This minimizes the chances for the cannula entangling with the suture threads. Thereafter the suture threads are released and the stiff cannula is advanced distally to straighten the pigtail loop and facilitate the removal of the catheter from the patient.

With some catheters the proximal end of the suture thread is locked or retained in place by placing a hollow cap onto or over the proximal end of the catheter tube after the suture thread has been drawn into a taut condition. This structure traps the proximal end of the suture thread. Any protruding portion of the suture thread can then be cut if desired. Trapping or locking the suture thread prevents the pigtail loop from straightening.

With other catheters the suture thread is trapped between two or more hollow tubes one of which is slidably inserted axially into the other. A short length of suture thread is generally left hanging from the catheter so that if it becomes loose, it may be retightened. For example, U.S. Pat. No. 5,041,085 to Osborne et al. discloses a lockable sleeve drainage catheter with a flexible distal end that can form a pigtail loop. A locking sleeve positioned at the proximal end of the catheter draws the suture thread through a passageway to retain the distal end in the pigtail configuration. A locking collar at the proximal end of the elongated member tube has an annular recess formed therein. An annular step at the distal end of the lockable sleeve engages the recess to lock the sleeve in a fixed position. When fully extended and locked, the sleeve and elongated member form a fluid tight connection to prevent any leakage of fluids being drained.

U.S. Pat. Nos. 4,643,720 and 4,740,195 to Lanciano disclose alternative embodiments of a mechanism specifically designed for retaining the distal end of a catheter in a pigtail loop. As particularly shown in the later patent, a suture thread, as a flexible link, extends through a member that, when rotated, wraps the suture thread about the circumference thereof. Consequently after the distal end of the catheter forms the pigtail loop, rotating the member tensions the suture thread to prevent the pigtail loop from straightening.

U.S. Pat. No. 5,419,764 to Roll discloses still another structure that incorporates a twisting lock. The twisting lock is positioned at the proximal end of the catheter to draw the suture thread or flexible link through the passageway of the catheter after the distal end of the flexible tube forms the pigtail loop. Twisting the proximal member relative to the distal member of the twisting locking device causes the suture to wrap around a reel within the device. Once the locking mechanism tightens the suture thread and reaches its locked position, a rubber O-ring is compressed resulting in a fluid tight connection. The friction exerted between the O-ring and the adjacent members prevents unlocking of the system and unwinding of the suture thread.

Controlling steerable catheters constitute another class of catheters with deflectable tips that use suture threads as flexible links, but for steering purposes. For example, U.S. Pat. No. 5,030,204 to Badger et al. discloses an axially displaceable manipulator that displaces a control line to deflect a distal tip and decrease the included angle between the distal portion and main portion of a shaft. Thus adjusting the control line position enables the catheter to steer the catheter by deflecting the catheter tip. U.S. Pat. No. 5,185,004 to Lashinski discloses another mechanism including a translational nut mechanism for limiting the number of turns that can be applied to a steerable guidewire. Stops to proximal and distal motion of the nut provide the limit.

Each of the foregoing Lanciano, Osborne et al. and Roll references discloses a locking or retention mechanism for maintaining the pigtail of a drainage catheter in a locked or retention position. However, each has certain disadvantages. For example, each of the retention mechanisms is formed as a housing with internally moving parts. The assembly of such mechanisms, particularly when it is desired to maintain a sealed environment, introduces complicated process or manufacturing steps that can increase the overall expense of the final catheter to prohibitive levels. Moreover, each involves locating a somewhat enlarged structure at the proximal end of the catheter that can be cumbersome to use and increase patient discomfort. Certain of these mechanisms are also subject to patient manipulation.

SUMMARY

Therefore it is an object of this invention to provide a retention mechanism for the flexible link or suture thread in a drainage catheter or the like that has a low profile and is compact thereby making the retention easy to use by a physician and reducing patient discomfort.

Another object of this invention is to provide a locking mechanism for a suture thread in a drainage catheter that includes a minimum number of components, particularly internal components.

Still another object of this invention is to provide a locking mechanism for the suture thread of a drainage catheter that minimizes the potential for the undesirable leakage of the drainage fluid therefrom.

Still another object of this invention is to provide a locking mechanism for a drainage catheter suture thread that is easy to manufacture.

In accordance with this invention a catheter includes an anchor at its distal end. The catheter comprises a flexible tube with a lumen extending between its proximal and distal ends. A flexible link extends through the lumen to control the configuration of the anchor by manipulation of the flexible link at the proximal end. A retention mechanism for preventing the displacement of the flexible link once it is in a locked position includes first and second bodies. The first body defines an axially extending passageway that communicates with the lumen in the flexible tube and attaches to the proximal end of the flexible tube so the flexible link extends through the passageway. The second body also has a passageway and can be axially displaced relative to the first body. Each of the first and second bodies have first and second interfitting means, respectively, for clamping the first and second bodies together and simultaneously clamping the flexible link to prevent its displacement.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
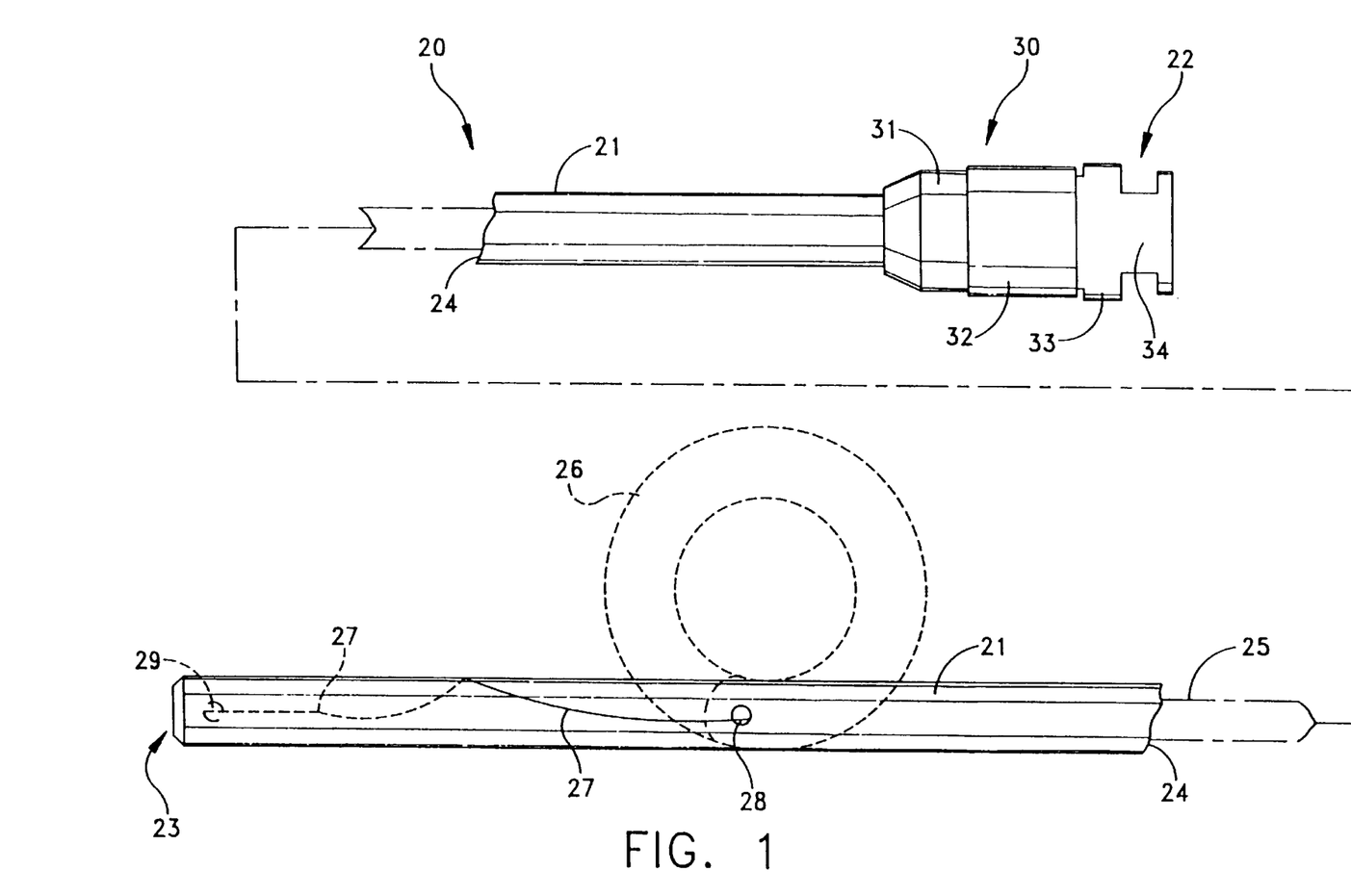
FIG. 1 is a view of a catheter that embodies this invention.

FIG. 1 depicts a catheter 20 with a radially flexible tube 21 that extends between a proximal end 22 and a distal end 23. A lumen 24 extends through the tube 21 and carries a flexible link 25 in the form of one or more suture threads. As shown by the solid lines in FIG. 1, the tube 21 extends along an axis when it is inserted and deflects into a pigtail loop 26 as shown by the dashed lines in FIG. 1 when a cannula or other straightening implement is removed from the lumen 24.

A distal end portion 27 of the suture thread 25 extends through a draw port or aperture 28 displaced from the distal end 23 and a draw port 29 or other connection at the distal end 23. If the suture thread 25 is loose when the pigtail loop formed, straightening the loop will draw additional suture thread to the space between the draw ports 28 and 29. After the pigtail loop 26 reforms, as known in the art, at least some of the additional suture thread must be withdrawn proximally to prevent forces from completely unwrapping the pigtail loop 26 to straighten the catheter 20.

A retention mechanism 30 according to this invention provides the locking action and is located at the proximal end 22. The retention mechanism can have any of several specific implementations. Each implementation, however, will include, in some form, a cap 31 and a distal body 32 that attach the retention mechanism 30 to the proximal end of the flexible tube 21. A proximal body 33 contains a standard fitting 34 such as a Leur fitting. Generally axial movement of the proximal body 33 with respect to the distal body 32 shifts the mechanism between a retention or locked configuration to an unlocked position. Moving the proximal body 33 to a locked position retains the suture thread 25 in place. In some embodiments this movement also takes up any slack in the suture thread 25.

More specifically, the cap 31 and distal body 32 constitute a first body that defines an axially extending internal passageway communicating with the lumen 24 through the flexible tube 21. The suture thread 25 acts as a flexible link that passes through this internal passageway. A second body comprising the proximal body 33 can be displaced axially relative to the first body. First and second interfitting structures formed in the distal body 32 and the proximal body 33 clamp the first and second bodies together and clamp portions of the suture thread 25 therebetween thereby to prevent displacement of the suture thread 25 and straightening of the pigtail loop 26.

Figure 2:
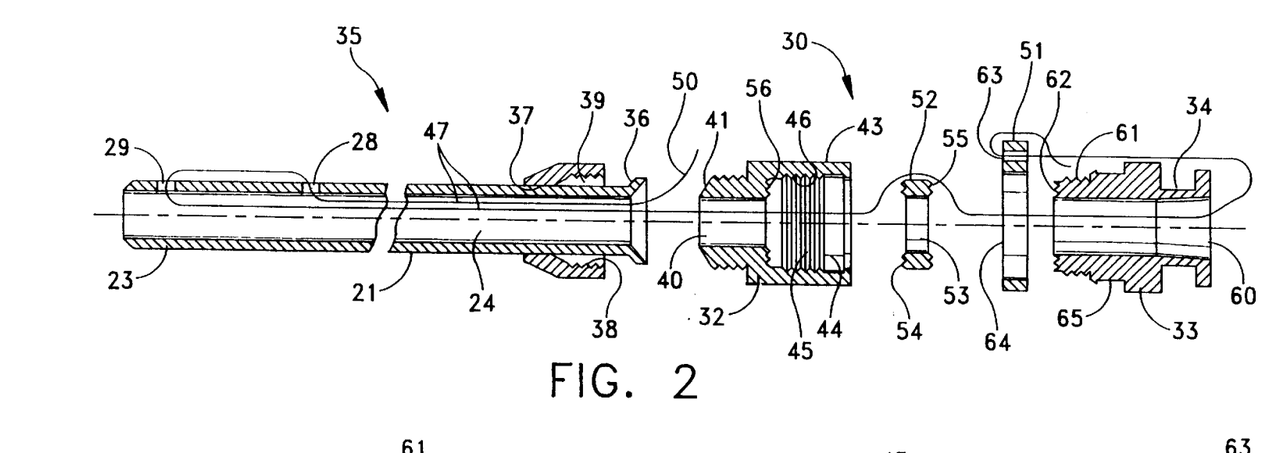
FIGS. 2 through 4 are various views that depict the construction and operation of one embodiment of this invention.
Figure 3:
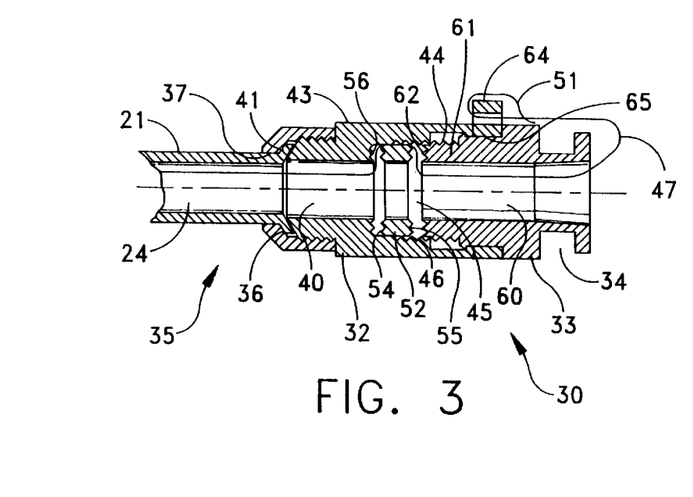
Figure 4:
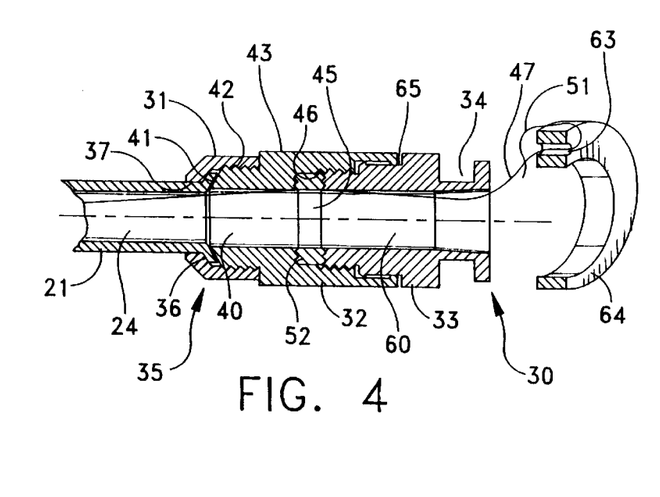

FIGS. 2 through 4 depict one specific embodiment in which a catheter 35 includes a flexible tube 21 that terminates, at its proximal end, in a flared end 36. A through aperture 37 of the end cap 31 allows it to slide over the flexible tube 21 to the flared end 36. Internal threads 38 are formed on the inner surface of a proximally facing cavity 39. The distal body 32 has a central axially extending main passage 40 from a bevelled proximal end 41. A threaded extension 42 mates with the cap 31 so that the bevelled end 41 engages the flared end 36. Tightening the end cap 31 so the internal threads 38 engage the threads 42 provides a seal between the combined end cap 31 and distal body 32 and the flexible tube 21. A proximal portion 43 of the distal body 32 defines a proximally directed cavity 44 with a central cavity 45 having internal threads 46.

As shown particularly in FIG. 2, the flexible link 25 of FIG. 2 is constituted by a suture 47 with a first end portion 50 captured between the end cap 31 and distal body 32. The main portion 47 of the suture extends distally through the draw port 28 and the draw port 29 and then returns proximally through the flexible tube 21 to exit the distal body 32 at an end 51. As will be apparent, pulling the end 51 after the pigtail loop reforms will draw loose portions and eventually tighten the thread. Assuming that 8 cm. of suture thread are displaced when the pigtail loop forms, 8 cm. of suture thread must be withdrawn from the proximal end before the suture thread 47 becomes taut.

In this embodiment the mechanism that retains the suture thread in the locking position comprises a grommet 52 that coacts with the distal body 32 and proximal body 33. The grommet 52 has a central aperture 53 and distal and proximal radial annular surfaces 54 and 55. The suture 47 is led outside the grommet 52. The grommet 52 can then be inserted into the cavity 45 until the radial annular surface 54 engages an end wall 56.

The proximal body 33 clamps the grommet 52 in position with either loose or clamping pressure. More specifically, the proximal body 33 includes a centrally located axially extending passage 60 and an externally threaded distal end 61 that terminates at a distal end surface 62. When the proximal body 33 is inserted into the distal body 32 and rotated, the end surface 62 engages the proximal radial annular surface 55 and drives the grommet 52 tightly against the end surface 56. As the suture 47 lies outside the grommet, but through the cavity 44 and passage 60, it is captured first between the surfaces 54 and 56 and between the surfaces 55 and 62. Each of these surfaces 56, 54, 55 and 62 can be roughened or otherwise modified to produce a surface with enhanced characteristics for gripping the suture 47 or other flexible link.

The free end 51 of the suture 47 is tied for convenience to an axial opening 63 formed in a C-ring spacer 64. The C-ring spacer 64 is adapted to clamp on an intermediate shank portion 65 of the proximal body 33.

The catheter is introduced in to the body as shown in FIG. 3, typically with a cannula (not shown) that prevents the distal end from forming the pigtail loop 26 in FIG. 1. After the catheter is introduced and located in the body, the cannula is removed and the pigtail forms. In the configuration of FIG. 3, the grommet 52 is loosely held in the cavity 45 so the physician can displace the suture 47 to move the distal end 23 of FIG. 2 into the pigtail loop by removing or slipping off C-ring spacer 64 and pulling it proximal till taut as shown in FIG. 4. Then the physician rotates the proximal body 33 until it clamps the grommet 52. At this point the distal radial surface 54 of the grommet 52 and end wall 56 of the distal body 32 and corresponding surfaces 55 and 62, as interfitting means, clamp the suture 47 and thereby prevent any straightening of the pigtail loop.

If, at a later time, it is desired to straighten the distal end portion 26, any connection to the Leur lock connector 34 can be removed. A cannula can then be inserted to the pigtail loop 26 while the suture threads are retained in their taut configuration. This reduces the likelihood of entangling the suture thread, if loose, with the cannula. Then the proximal body 33 can be unscrewed to release the clamping action and the cannula then can be advanced further to straighten the pigtail loop 26 in the distal end portion 23 and enable the catheter 35 to be removed from the patient.

Figure 5:
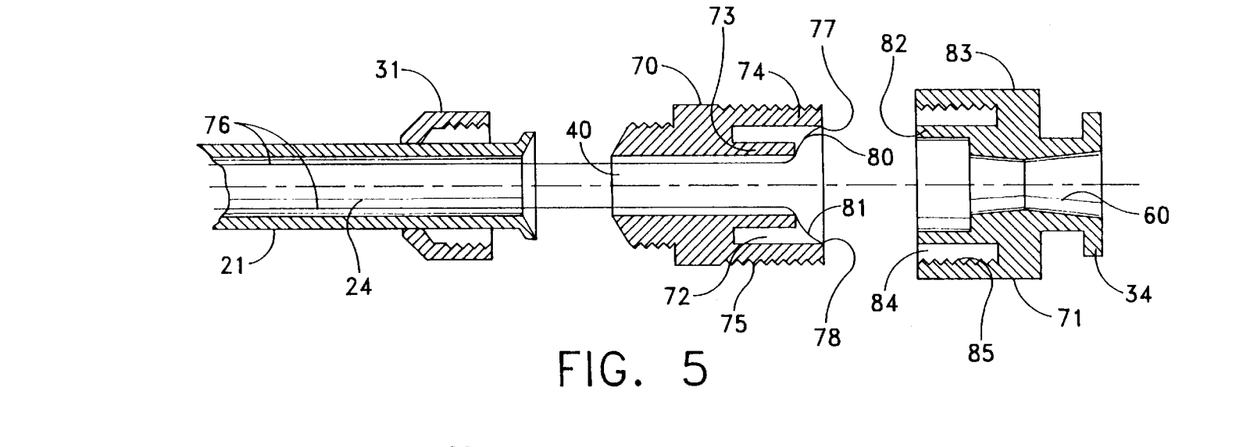
FIGS. 5 through 7 are various views that depict the construction and operation of a second embodiment of this invention.
Figure 6:
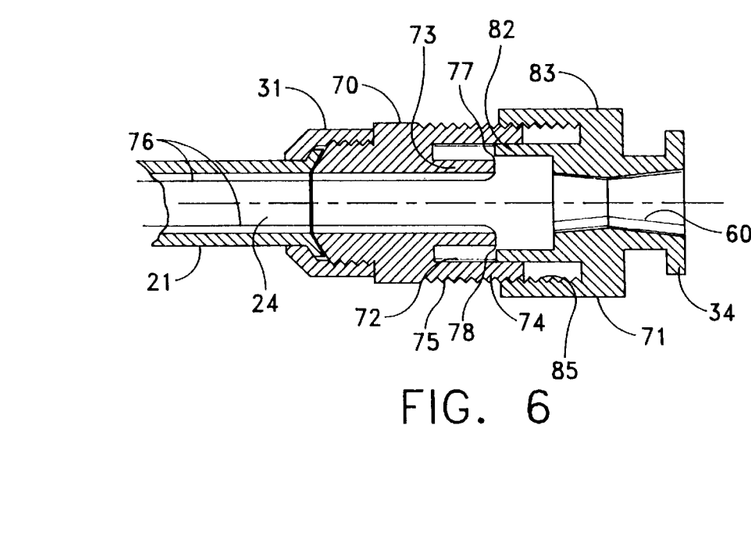
Figure 7:
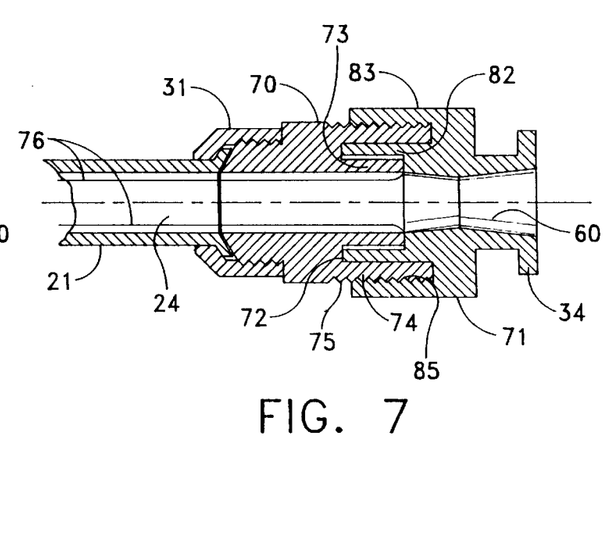

FIGS. 5 through 7 depict an alternative embodiment which includes an end cap 31, a distal body 70 and a proximal body 71. As will become apparent, this structure eliminates any need for a physician to grasp a suture. Each centimeter displacement of the proximal body 71 takes up four centimeters of slack in the suture thread.

In this embodiment, as in the embodiment of FIGS. 2 through 4, the end cap 31 and the distal end of the distal body 70 form a seal that captures the proximal end of the flexible tube 21. The distal body 70 includes the central passage 40; the proximal body 71 includes the central passage 60. The passages 40 and 60 form a continuation of the lumen 24 through the flexible tube 21.

The distal body 70 in this embodiment has a proximally facing axially extending cavity 72 that is concentric with the central passage 40. It is defined by a central cylindrical extension 73 in the form of an annular barrier and radially spaced therefrom a cylindrical extension 74 with external threads 75 from the proximal edge thereof.

The tension member is constituted by a suture 76 that has opposite ends 77 and 78 attached to the proximal edge of the distal body 70. Portions of 80 and 81 at the opposite ends 77 and 78, respectively, extend radially across the cavity 72 into the central passage 40.

The proximal body 71 has two radially spaced, concentric cylindrical extensions 82 and 83 that define extensions of the central passage 60 and a proximally facing cylindrical annular cavity 84. The relative spacings of the different counterfacing components on the distal body 70 and the proximal body 71 provide an interfitting structure because the cavity 84 is radially aligned with the exterior cylinder 74 and the cavity 72 is radially aligned with the inner cylindrical barrier 82. The outer cylindrical extension 83 on the proximal body 71 has internal threads 85 for engaging the external threads 75.

As assembled in the configuration shown particularly in FIG. 6, the exterior cylinder 74 has entered the cavity 84 while the interior cylinder 82 is aligned with the cavity 72. At this point the suture portions 80 and 81 extend across the face of the inner cylinder 82 and the distal end of the catheter is in an extended position as shown by solid lines in FIG. 1.

After insertion in a patient and formation of a pigtail loop, the proximal body 71 can be rotated relative to the distal body 82 so the proximal body 71 advances distally with respect to the distal body 70. As this occurs, the suture portions 80 and 81 are driven into the cavity 72 and fold over the inner cylinder 82 thereby displacing each of the suture portions 80 and 81 by two times the axial length of the cylinder 82. Thus each centimeter of axial displacement of the proximal body 71 also will displace a total of four centimeters of slack suture thread.

Figure 8:
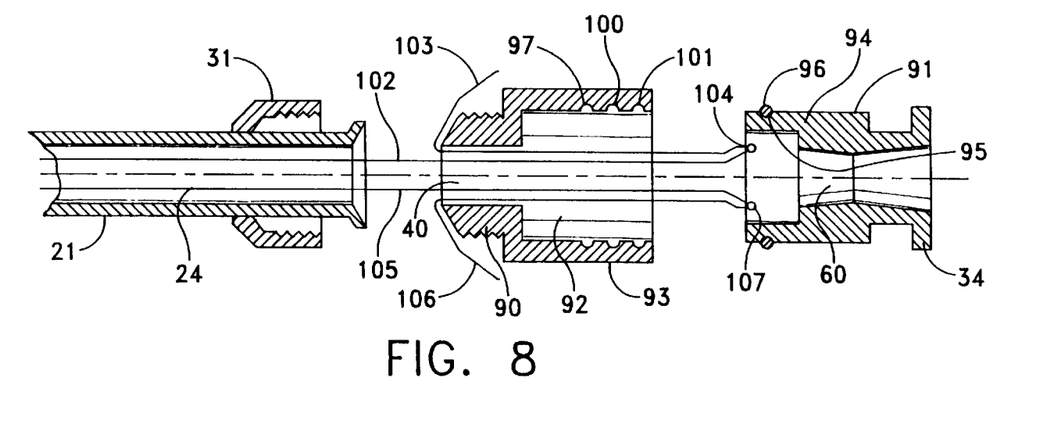
FIGS. 8 through 10 are views that depict the construction and operation of a third embodiment of this invention.
Figure 9:
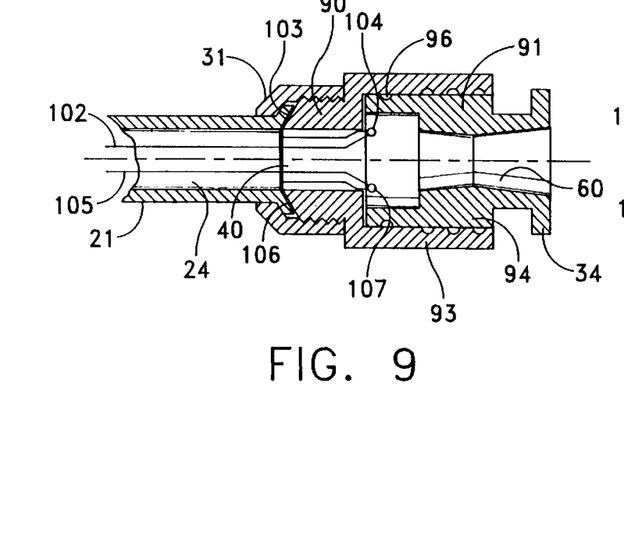
Figure 10:
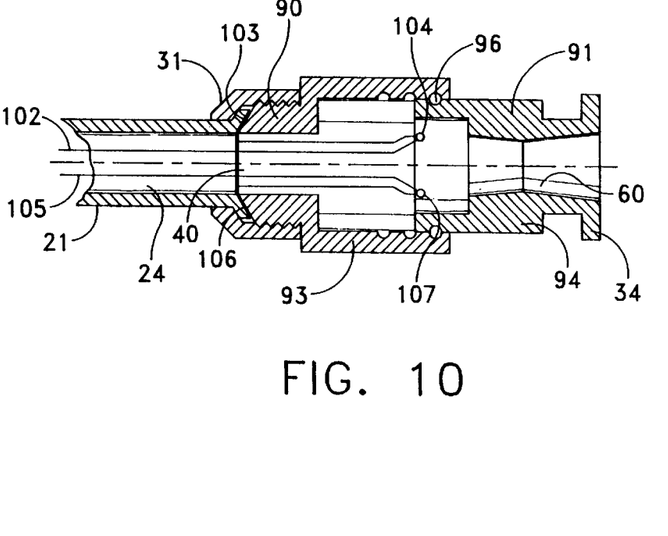

As stated above, FIGS. 5 through 7 depict a mechanism in which distal motion of the proximal body 71 take up the slack in the suture thread after the pigtail loop forms. FIGS. 8 through 10 depict an alternative embodiment including a distal body 90 and proximal body 91. In this embodiment proximal motion of the proximal body 91 takes up the slack in the suture thread. The distal body 90 has a single proximally facing cavity 92 formed by a cylindrical shell 93 that defines an extension of the passageway 40. The proximal body 91 has a distally extending body 94 that forms the passage 60 and has an outer diameter that corresponds to the inner diameter of the cylindrical shell 93.

As shown particularly in FIG. 8, an external circumferential groove 95 is formed at the distal end of the cylindrical body 94. A sealing O-ring 96 is held in the groove 95. The interior surface of the cylindrical shell 93 has three axially spaced circumferential grooves 97, 100 and 101. These grooves act with the O-ring 96 to produce a series of detent positions.

The flexible link in this embodiment includes a first suture strand 102 having an end 103 clamped between the end cap 31 and the distal body 90. The suture strand 102 passes through an aperture 104 formed at the distal end of the proximal body 91. The suture strand 102 extends to the distal end of the catheter for passage through ports like the draw ports 28 and 29 in FIGS. 1 and 2. The continuation of the suture forms a second strand 105 that extends to a second end 106 through a second aperture 107. The end 106 also is clamped between the end cap 31 and the distal body 90.

FIG. 9 depicts the distal body 90 and proximal body 91 in a fully nested position. As previously indicated in this configuration the distal end of the flexible tube 21 can be in a straightened position. After the pigtail loop forms, the proximal body 91 moves proximally (i.e., to the right in FIGS. 8 through 10) to take up the slack in the suture thread. It will be apparent that, for each centimeter, the proximal body 91 takes up four centimeters of slack. Consequently a two-centimeter displacement of the proximal body 91 is all that is necessary to take up the normal eight centimeters of slack and lock the distal end of the catheter in the pigtail loop.

As the proximal body 91 continues to move distally, the O-ring 96 will engage the groove 97 to produce a first detent position. The detent action will be sufficient to signal the arrival of the proximal body 91 at the corresponding position. Slight additional tension or force applied proximally will cause the O-ring to release from the groove 97. When the O-ring 96 reaches the grooves 100 and 101 respectively and consecutively, additional detenting action will occur with corresponding tactile signals being transferred to the physician. Appropriate calibration of the detents can be provided to control partial closure of the pigtail loop or other anchoring device.

Figure 11:
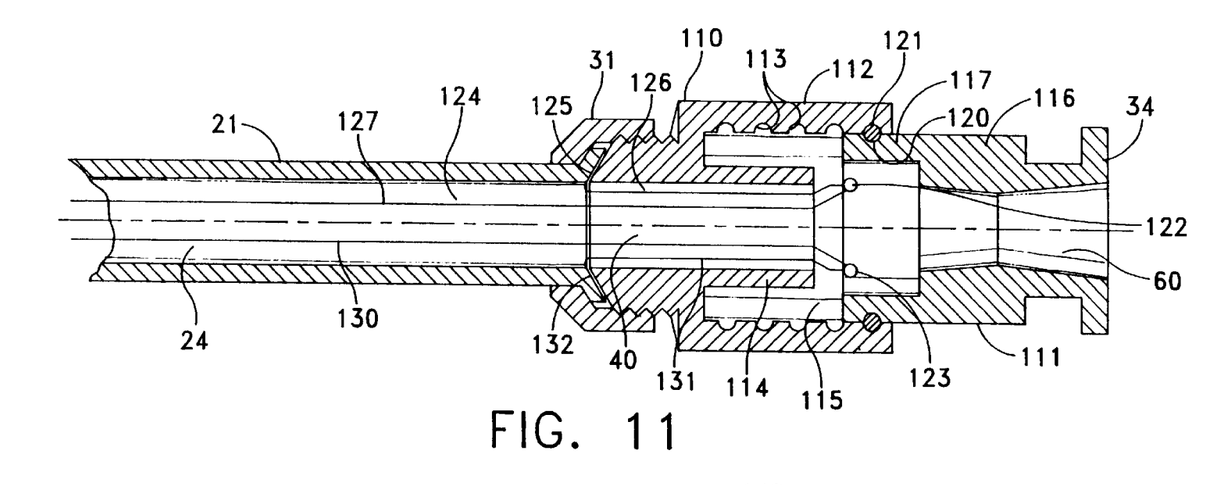
FIG. 11 is a view that depicts a fourth embodiment of this invention.

FIG. 11 depicts a variation that combines elements of the displacement mechanisms of the embodiment of FIGS. 5 through 7 and elements of the detent mechanism of the embodiment of FIGS. 8 through 10. More specifically, FIG. 11 depicts the end cap 31 that captures the flexible tube 21 in a distal body 110 that forms the passage 40 as an extension of the lumen 24. A proximal body 111 forms the passage 60 as an additional extension of the lumen 40 and that terminates in the connector 34.

The distal body 110 has an outer cylindrical shell body 112 with a series of axially spaced, internal, circumferential grooves 113 formed therein. A central, annular, cylindrical element 114 forms an extension of the passage 40 and is spaced from the body 112 to form a proximally facing annular cavity 115.

The proximal body 111 includes a central body 116 and a distally extending open shell cylinder 117 that is aligned with the cavity 115. A groove 120 at the distal end of the cylinder 117 carries an O-ring 121 that engages each of the grooves 113 in succession. The proximal body 111 also includes apertures 122 and 123 at the distal edge thereof. In accordance with this embodiment a single suture 124 extends between the proximal and distal ends of the catheter. A first end 125 is clamped between the end cap 31 and the distal body 110. A section 126 of the suture 124 leads proximally to the draw port 122 and then to the distal end to another draw port such as the draw port 29 in FIG. 2. Another portion or strand of the suture 130 returns from the distal end through the draw port 123 to form a portion 131 extending to an end 132 also captured between the end cap 31 and the distal body 110.

The cylindrical element 117 interfits with the distal body 110 by being displaced distally into the cavity 115. As this occurs, each of the apertures 122 and 123 through which the suture 124 is reeved defines a two-part link. Thus, in this embodiment, a one-centimeter displacement of the proximal body 111 takes up four centimeters of slack of the suture thread, i.e., two centimeters in each of the portions 127 and 130. Thus the embodiment of FIG. 11, like the embodiment in FIGS. 5 and 6, produces a corresponding displacement using distal motion of the proximal member 111, but uses a detent structure as shown in FIGS. 8 and 9.

Figure 12:
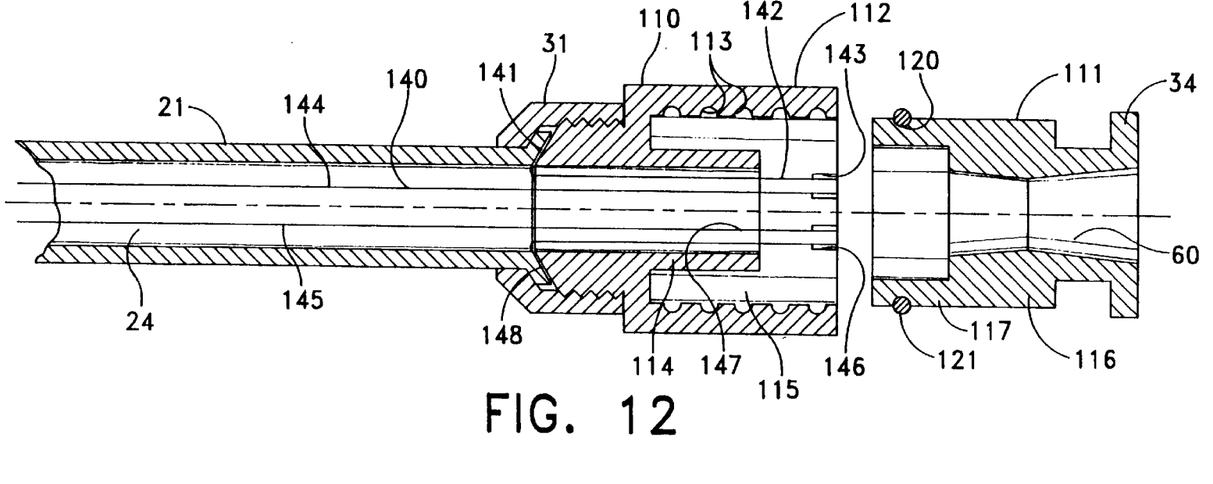
FIG. 12 is a view that depicts a fifth embodiment of this invention.

FIG. 12 depicts another embodiment using a variation on the structure shown in FIG. 11 so like reference numerals define like elements. More specifically, the embodiment in FIG. 12 includes the end cap 31 attached to the distal body 110 for receiving a proximal body 111 with a detent mechanism. In this embodiment a suture 140 has a first end 141 clamped between the end cap 31 and distal body 110. In a fashion analogous to that shown in FIG. 11 a portion 142 of the suture extends from the end 141 through an aperture 143 and then distally as a strand 144 to the distal tip. A return strand 145 passes through a second aperture 146 and continues as a second end portion 147 to a second end 148 clamped between the end cap 31 and the distal body 110. The apertures 143 and 146 are mounted at the proximal edge of the external cylinder 112 so that the suture portions reeved through the apertures 143 and 146 displace radially across the cavity 115. Consequently as the proximal body 111 advances distally one centimeter, it will take up eight centimeters of slack in the suture thread portions 144 and 145 produced when the pigtail loop forms.

Figure 13:
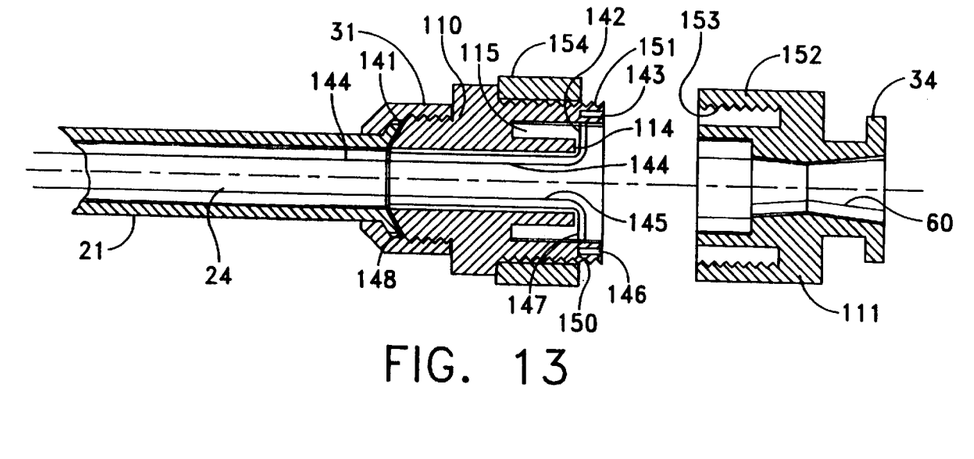
FIG. 13 is a view that depicts a sixth embodiment of this invention.

FIG. 13 depicts another embodiment having the same general form as FIG. 12. The suture thread portion 144 has ends 141 and 148 clamped between the end cap 131 and the distal body 110. Portions 142 and 144 extend through an aperture 143 and portions 145 and 147 extend through an aperture 146. In this embodiment, the apertures 143 and 146 lie on opposite sides of a cylindrical outer extension 150 that replaces the outer cylindrical portion 112 in FIG. 12. The cylinder 150 has external threads 151, a corresponding portion 152 of the proximal body 111 has internal threads 153. In this particular embodiment a spacer 154 is positioned at the proximal end of the thread 151. This enables the proximal body 111 to be threaded part way along the distal body 110. Once the catheter has been inserted in a patient and the pigtail loop forms, the proximal member 111 can be backed off to loosen and allow removal of the spacer 154, that can have the configuration of a C-ring, thereby to enable the proximal member 111 to be screwed onto the distal body 110 driving the suture portions 142, 144, 145 and 147 into the cavity 115 to take up eight centimeters of slack in the suture for each centimeter of displacement of the proximal body 111.

Figure 14:
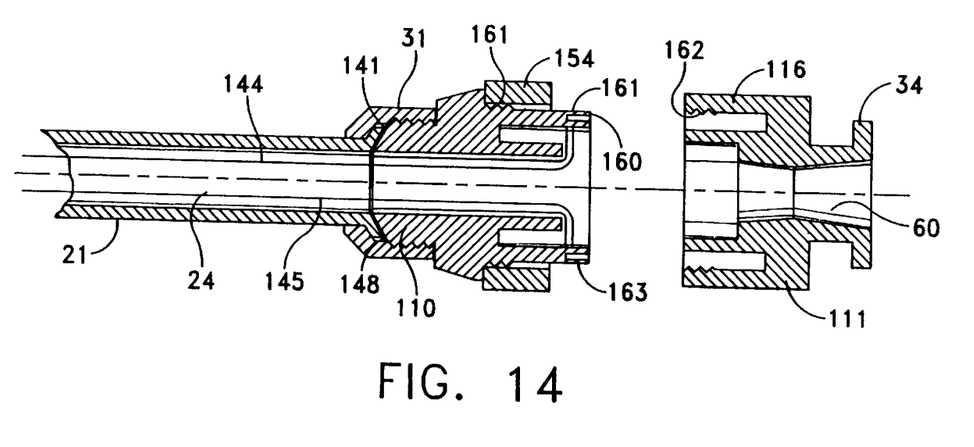
FIG. 14 is a view that depicts a seventh embodiment of this invention.

FIG. 14 depicts another embodiment in the form of a variation of FIG. 13. In this particular embodiment the distal body 110 has an outer, proximally facing cylinder 160 with threads 161 only over a distal portion of the surface of the member 161. A spacer 154, like the spacer in FIG. 13, overlies the threads 152 and produces a standoff for the proximal body 111 that includes internal threads 162 only along a distal portion of the outer cylinder 116. The suture 144 has the same form as the suture in FIG. 13. A single thread or retaining ridge 163 at the proximal end of the distal body 110 keeps the proximal body 111 on the distal body 110 for shipment. In use, a physician removes the spacer 154 and displaces the proximal body 111 in a distal direction without rotating the proximal body 111 until the threads initially engage. Thereafter the physician rotates the proximal body 111 to further engage threads and advance the proximal body in a distal direction. This speed lock approach provides a very rapid method of taking up the slack while still providing sufficient friction through the threads to prevent unlocking of the pigtail loop.

Figure 15:
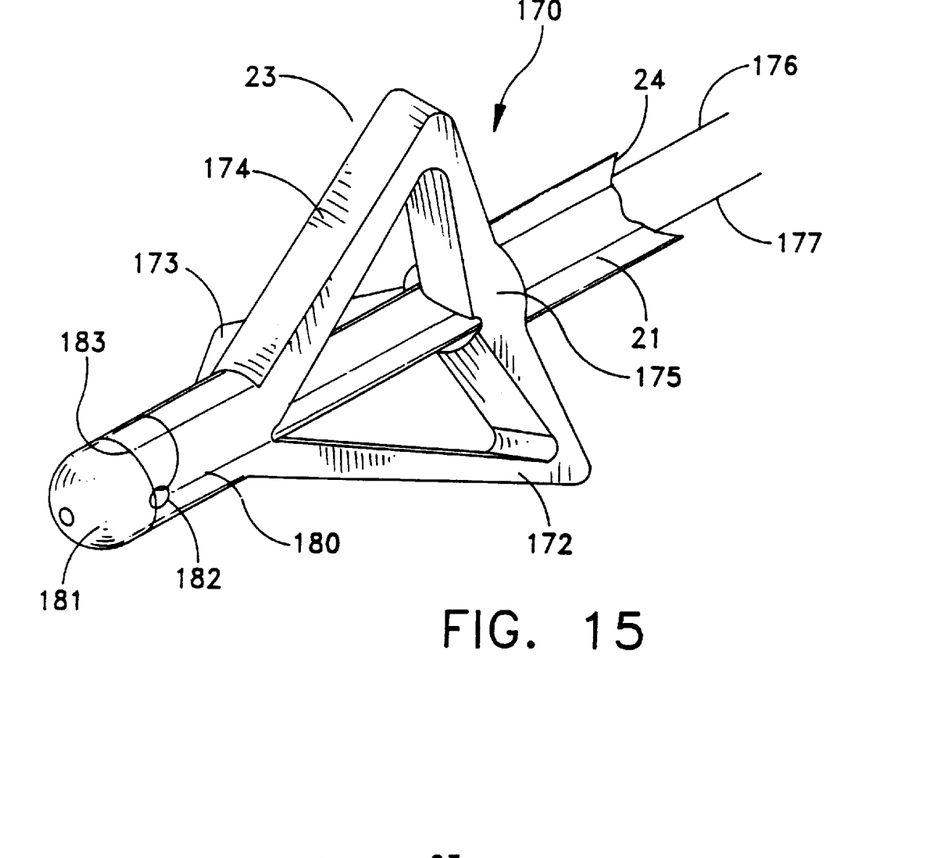
FIG. 15 depicts an alternative anchor for use with apparatus constructed in accordance with this invention.
Figure 16:
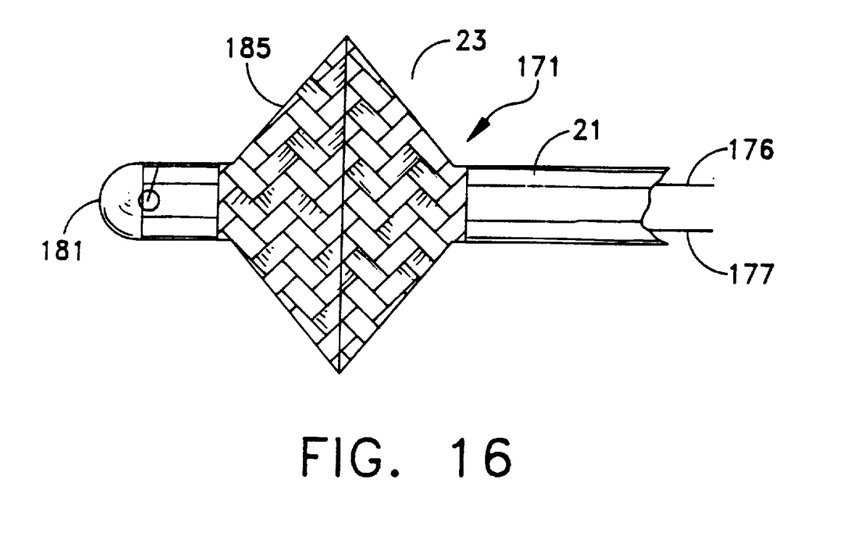
FIG. 16 depicts another anchor for use with apparatus constructed in accordance with this invention.

Each of the foregoing embodiments has been described for locking a pigtail loop as an anchor. Other devices also can serve as catheter anchors. FIG. 15, for example, depicts a tulip anchor 170; FIG. 16, a foraminous anchor 171. Each anchor is formed at the distal end 23 of the catheter flexible tube 21.

The tulip anchor 170 in FIG. 15 is formed of a memory material with three radial arms 172, 173 and 174 equiangularly spaced about the flexible tube and longitudinally extending. They are attached at a proximal base 175. Normally the arms extend from the base 175 as shown in FIG. 15. A central point 180 of the suture threads 176 and 177 is located on a nose portion 181 that attaches to the distal end of the radial arms 172, 173 and 174. The suture thread exits a port 182 at the nose 181, forms a full turn 183 and then returns through the lumen 24 through another port diametrically opposite the port 182. This effectively locks the suture thread to the nose 181. During the insertion process a cannula is extended through the lumen 24 to engage the nose 181 and displace the nose 181 distally with respect to the base 175. This moves the arms radially toward the center to produce a compact form. A pair of suture thread portions 176 and 177 extend through the lumen 24.

The suture thread portions 176 and 177 extend to any of the mechanisms as shown in FIGS. 5 through 14. When the cannula is removed, the arms 172, 173 and 174 reform by deflecting radially to form a full anchoring structure as shown in FIG. 15. This action introduces slack in the suture threads 176 and 177 that also connect to any of the foregoing mechanisms. If the mechanism is as shown in FIGS. 5 through 7 or FIG. 11, a one-centimeter distal movement of the proximal body 33 will take up the slack introduced by a two-centimeter proximal movement of the nose 181 relative to the base 175. The same one-centimeter displacement of the proximal body 91 in FIGS. 8 through 10 in the proximal direction takes up the slack introduced by a two-centimeter proximal movement of the nose 181 relative to the base 175. In the mechanisms in FIGS. 12 through 14 a one-half-centimeter distal movement of the proximal body 34 will take up the slack introduced by a two-centimeter proximal movement of the nose 181 relative to the base 175.

The foraminous anchor 171 in FIG. 16 has a similar construction to the tulip anchor 170 in FIG. 15 except that a woven sleeve 185 replaces the radial arms 173 through 174. When the nose 181 is extended distally by a cannula, the sleeve 185 has a generally cylindrical form with an outer diameter corresponding to the diameter of the flexible tube 21. When the anchor forms, any of the foregoing mechanisms will take up the slack in the suture threads 176 and 177. The same ratios of take up to displacement of the mechanism at the proximal end will occur as described with respect to the tulip anchor in FIG. 15.

In summary, each of the foregoing embodiments has certain common characteristics. Each locking mechanism comprises a first body and a second body such as the distal body 32 and proximal body 33 in FIGS. 1 through 4, the distal and proximal body 70 and 71 in FIGS. 5 through 7, 90 and 91 in FIGS. 8 through 10, 110 and 111 in FIGS. 11 through 14. In each the first body, typically the distal body, defines an axially extending passageway 40 in communication with the lumen 24 of the flexible tube. An end cap or like device attaches the proximal end of the flexible tube to the first body. Moreover in each a flexible link in the form of a suture comprising two strands or parts of a single suture thread extend through the passageway 40. Each second body has a passageway 60. Each of the first and second bodies have first and second interfitting means for clamping the first and second body means together and clamping the tension member therebetween.

In FIGS. 1 through 4 the interfitting means include the grommet 52 that clamps against both the end surfaces 56 and 62 with the adjacent threads producing a locking action to prevent inadvertent displacement of the two bodies. In each of the remaining figures each of the bodies includes counterfacing radially spaced offset cylindrical elements that produce intermediate cavities for receiving complementary elements such that proximal and distal bodies interfit. In the particular embodiments of FIGS. 1 and 4 the embodiment does not displace the suture but merely clamps it. In the remaining embodiments of FIGS. 5 through 14 the proximal and distal bodies perform both displacement and locking functions.

This invention has also been described with respect to anchors formed by pigtail loops in the catheter or by tulip or foraminous anchors. Other known anchor structures, such as Malecot and Amplatz anchors, are also readily adapted for use with this invention.

Thus, this invention has been disclosed in terms of diverse embodiments. It will be apparent that many other modifications can be made to the disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. A catheter comprising:
    a tube having a proximal end, a distal end, and an anchor at the distal end;
    a first body for engagement with the proximal end of said tube;
    a second body relatively displaceable with respect to the first body to engage the first body; and
    a flexible link operable to control a configuration of said anchor, the link extending from the anchor through the tube to the first and second bodies, the engagement of the first and second bodies preventing the flexible link from moving relative to the tube.

2. The catheter of claim 1, further comprising a connecting member disposed on the proximal end of the tube and configured to selectively engage the first body.

3. The catheter of claim 2, wherein the first body includes a first threaded portion and the connecting member is rotatably disposed on the tube and includes a threaded portion configured to engage the first threaded portion of the first body.

4. The catheter of claim 3, wherein the flexible link comprises a suture thread and one end of the suture thread is clamped between the first body and the connecting member.

5. The catheter of claim 1, wherein the second body includes a coupling member configured to connect the catheter to an external device.

6. The catheter of claim 1, wherein the first body includes a first interfitting structure and the second body includes a second interfitting structure configured to engage the first interfitting structure.

7. The catheter of claim 6, further comprising an annular grommet disposed between the first and second bodies, the flexible link extending outside the grommet such that engagement of the first and second interfitting structures clamps the flexible link between the grommet and the first and second interfitting structures.

8. The catheter of claim 7, wherein the grommet includes roughened surfaces.

9. The catheter of claim 1, further comprising a spacer disposable between the first and second bodies to maintain a predetermined displacement between the first and second bodies.

10. The catheter of claim 1, wherein the first and second bodies include complementary threaded portions and rotation of the second body with respect to the first body axially displaces the second body with respect to the first body.

11. The catheter of claim 1, wherein the first and second bodies include complementary detent portions configured to establish first and second axial positions of the second body with respect to the first body.

12. The catheter of claim 1, wherein axial movement of the second body with respect to the first body displaces the flexible link with respect to the tube, thereby altering the configuration of the anchor.

13. The catheter of claim 12, wherein the second body includes an axially extending annular protrusion, the first body includes an annular recess configured to receive the annular protrusion of the second body, and the flexible link transverse the recess of the first body such that axial displacement of the second body with respect to the first body causes said annular protrusion to engage and displace the flexible link relative to the tube.

14. The catheter of claim 13, wherein axial movement of the second body with respect to the first body creates at least one fold in the flexible link such that the displacement of the flexible link with respect to the anchor is a multiple of the displacement of the second body with respect to the first body.

15. The catheter of claim 13, wherein the flexible link comprises a suture thread forming a loop between the proximal end of the tube and the anchor, such that both ends of the suture thread extend to the proximal end of the tube.

16. The catheter of claim 15, wherein both ends of the suture thread are attached to the first body and traverse the annular recess in the first body and axial movement of the second body with respect to the first body creates two folds in the flexible link such that the displacement of the flexible link with respect to the anchor is a multiple of the displacement of the second body with respect to the first body.

17. A locking mechanism for a catheter having a tube including a proximal end, a distal end, and an anchor at the distal end, the locking mechanism comprising:

a first body for engagement with the proximal end of said tube;

a second body relatively displaceable with respect to the first body to engage the first body; and a flexible link operable to control a configuration of said anchor, the flexible link extending form the anchor through the tube to the first and second bodies, the engagement of the first and second bodies preventing the flexible link from moving relative to the tube.

18. The locking mechanism of claim 17, wherein the first body includes a first interfitting structure and the second body includes a second interfitting structure configured to engage the first interfitting structure.

19. The locking mechanism of claim 18, further comprising an annular grommet disposed between the first and second interfitting structures, the flexible link extending outside the grommet such that engagement of the first and second interfitting structures clamps the flexible link between the grommet and the first and second interfitting structures.

20. The locking mechanism of claim 19, wherein the grommet includes roughened surfaces.

21. The locking mechanism of claim 17, further comprising a spacer disposable between the first and second bodies to maintain a predetermined displacement between the first and second bodies.

22. The locking mechanism of claim 17, wherein the first and second bodies include complementary threaded portions and rotation of the second body with respect to the first body axially displaces the second body with respect to the first body.

23. The locking mechanism of claim 17, wherein the first and second bodies include complementary detent portions configured to establish first and second axial positions of the second body with respect to the first body.

24. The locking mechanism of claim 17, wherein axial movement of the second body with respect to the first body displaces the flexible link with respect to the tube, thereby altering the configuration of the anchor.

25. The locking mechanism of claim 24, wherein the second body includes an axially extending annular protrusion, the first body includes an annular recess configured to receive the annular protrusion of the second body, and the flexible link traverses the recess of the first body such that axial displacement of the second body with respect to the first body causes said annular protrusion to engage and displace the flexible link relative to the tube.

26. The locking mechanism of claim 25, wherein axial movement of the second body with respect to the first body creates at least one fold in the flexible link such that the displacement of the flexible link with respect to the anchor is a multiple of the displacement of the second body with respect to the first body.

27. The locking mechanism of claim 25, wherein the flexible link comprises a suture thread forming a loop between the proximal end of the tube and the anchor, such that both ends of the suture thread extend to the extend to the proximal end of the tube.

28. The locking mechanism of claim 27, wherein both ends of the suture thread are attached to the first body and traverse the annular recess in the first body and axial movement of the second body with respect to the first body creates two folds in the flexible link such that the displacement of the flexible link with respect to the anchor is a multiple of the displacement of the second body with respect to the first body.

* * * * *

UNITED STATES PATENT AND TRADEMARK OFFICE
CERTIFICATE OF CORRECTION

PATENT NO.: 6,042,577

DATED: March 28, 2000

INVENTOR(S): Chu et al.

It is certified that an error appears in the above-identified patent and that said Letters Patent is hereby corrected as shown below:

Claim 17, col. 12, line 4, "form" should read --from--.

Signed and Sealed this

Twentieth Day of February, 2001

Attest:

NICHOLAS P. GODICI

Attesting Officer     Acting Director of the United States Patent and Trademark Office